United States Patent
Ryan

(10) Patent No.: US 6,200,500 B1
(45) Date of Patent: Mar. 13, 2001

(54) HEMATOLOGY CONTROL AND SYSTEM FOR MULTI-PARAMETER HEMATOLOGY MEASUREMENTS

(75) Inventor: Wayne L. Ryan, Omaha, NE (US)

(73) Assignee: Streck Laboratories, Inc., La Vista, NE (US)

( * ) Notice: Subject to any disclaimer, the term of this patent is extended or adjusted under 35 U.S.C. 154(b) by 0 days.

(21) Appl. No.: 09/378,608

(22) Filed: Aug. 20, 1999

(51) Int. Cl.$^7$ ..................................................... G01N 31/00
(52) U.S. Cl. ............................. 252/408.1; 436/8; 436/10; 436/16
(58) Field of Search ............................. 252/408.1; 436/8, 436/10, 15, 16, 17, 18

(56) References Cited

U.S. PATENT DOCUMENTS

| | | |
|---|---|---|
| 3,558,522 | 1/1971 | Louderback et al. . |
| 3,574,137 | 4/1971 | Decasperis et al. . |
| 3,607,783 | 9/1971 | Tata . |
| 3,640,896 | 2/1972 | DeCasperis . |
| 3,873,467 | 3/1975 | Hunt . |
| 4,099,917 | 7/1978 | Kim . |
| 4,160,644 | 7/1979 | Ryan . |
| 4,179,398 | 12/1979 | Hunt . |
| 4,198,206 | 4/1980 | Ryan . |
| 4,219,440 * | 8/1980 | Runck et al. . |
| 4,264,470 | 4/1981 | Chastain, Jr. et al. . |
| 4,299,726 | 11/1981 | Crews et al. . |
| 4,324,686 | 4/1982 | Mundschenk . |
| 4,324,687 | 4/1982 | Louderback et al. . |
| 4,358,394 | 11/1982 | Crews et al. . |
| 4,389,490 | 6/1983 | Crews et al. . |
| 4,390,632 | 6/1983 | Carter, II . |
| 4,425,334 | 1/1984 | Hunt . |
| 4,436,821 * | 3/1984 | Ryan . |
| 4,579,824 * | 4/1986 | Louderback et al. . |
| 4,698,312 * | 10/1987 | Wong et al. . |
| 4,704,364 | 11/1987 | Carver et al. . |
| 4,711,852 | 12/1987 | Jacobson et al. . |
| 4,745,071 | 5/1988 | Lapicola et al. . |
| 4,751,179 | 6/1988 | Ledis . |
| 4,777,139 * | 10/1988 | Wong et al. . |
| 5,008,021 | 4/1991 | Conner et al. . |
| 5,008,201 * | 4/1991 | Ryan . |
| 5,262,327 | 11/1993 | Ryan . |
| 5,270,208 * | 12/1993 | Ryan . |
| 5,320,964 | 6/1994 | Young et al. . |
| 5,432,089 * | 7/1995 | Ryan et al. . |
| 5,459,073 | 10/1995 | Ryan . |
| 5,460,797 | 10/1995 | Ryan . |
| 5,492,833 | 2/1996 | Rodriguez et al. . |
| 5,529,933 | 6/1996 | Young et al. . |
| 5,616,501 | 4/1997 | Rodriguez et al. . |
| 5,672,474 | 9/1997 | Ryan . |
| 5,677,145 | 10/1997 | Ryan . |
| 5,731,205 | 3/1998 | Ryan . |
| 5,736,402 * | 4/1998 | Francis et al. . |
| 5,811,099 | 9/1998 | Ryan . |
| 5,811,303 * | 9/1998 | Ryan . |
| 5,858,789 * | 1/1999 | Francis et al. . |
| 5,858,790 * | 1/1999 | Kim et al. . |
| 5,888,790 | 5/1999 | Cahoon et al. . |
| 5,939,326 * | 8/1999 | Chupp et al. . |
| 5,945,340 * | 8/1999 | Francis et al. . |
| 5,981,282 * | 11/1999 | Ryan . |
| 5,994,139 * | 11/1999 | Jacobs et al. . |
| 6,060,322 * | 5/2000 | Horton et al. . |
| 6,074,879 * | 6/2000 | Zelmanovic et al. . |

FOREIGN PATENT DOCUMENTS

| | | |
|---|---|---|
| WO 93/17329 | 9/1993 | (WO) . |
| WO 93/17330 | 9/1993 | (WO) . |

OTHER PUBLICATIONS

Copending Application Serial No. 09/315,335, filed May 20, 1999, White Blood Cell Hematology Control.

Copending Application Serial No. 09/390,953, filed Sep. 7, 1999, White Blood Cell Hematology Control.

Copending Application Serial No. 09/015,567, filed Jan. 30, 1998, White Blood Cell Hematology Control.

Greenfield, S.M. et al., "Inhibition of Red Cell Membrane Lipid Peroxidation by Sulphasalazine and 5–Aminosalicylic Acid," *Gut* 32:1156–1159 (1991). (no month).

Lombarts, A.J.P.F. et al., "A Stable Human Platelet–White Blood Cell Control for the Coulter Model S–Plus II," *Clinica. Chimica. Acta.* 130:95–102 (1982). (no month).

Lombarts, A.J.P.F. et al., "A White Blood Cell Control of Long–Term Stability," *Clinica. Chimica. Acta.* 129:79–83 (1983). (no month).

Negre–Salvayre, A. et al., "Protective Effect of a–Tocopherol, Ascorbic Acid and Rutin against Peroxidative Stress Induced by Oxidized Lipoproteins on Lymphoid CellLines," *Biochem. Pharmacol.* 42:450–453 (1991). (no month).

Sorette et al., "Improved Isolation of Normal Human Reticulocytes via Exploitation of Chloride–Dependent Potassium Transport," *Blood*, vol. 80, No. 1, (Jul. 1, 1992); pp. 249–254.

\* cited by examiner

*Primary Examiner*—Deborah Jones
*Assistant Examiner*—Jennifer McNeil
(74) *Attorney, Agent, or Firm*—Dobrusin Darden Thennisch & Lorenz PLLC

(57) ABSTRACT

Hematology control compositions and systems used to measure a plurality of parameters in a blood sample are provided. The hematology control compositions are particularly useful as a control for multi-parameter, automated instrument systems. The control compositions comprise a reticulocyte component, a white blood cell component, a red blood cell component, a nucleated red blood cell component, a platelet component and a reticulated platelet component. Methods of making and using the control compositions are also provided.

32 Claims, No Drawings

HEMATOLOGY CONTROL AND SYSTEM FOR MULTI-PARAMETER HEMATOLOGY MEASUREMENTS

FIELD OF THE INVENTION

The present invention relates generally to hematology control compositions and systems and, more particularly, to a hematology control composition and system used to measure a plurality of parameters in a sample of blood with a multi-parameter automated hematology instrument.

BACKGROUND OF THE INVENTION

Hematology controls for various automated instruments that measure, for example, red and white blood cell counts and platelet counts, are known in the art and are described in the following U.S. Pat. Nos.: 3,558,522; 3,873,467; 4,179,398; 4,219,440; 4,299,726; 4,324,687; 4,358,394; and 4,436,821 (incorporated by reference herein). Currently, blood analysis requires the use of one or more of several different instruments and, subsequently, different blood samples and blood sample preparations to analyze the various components of blood. Several hematology instruments, however, now have the capability of measuring various parameters of blood without requiring separate sample preparation for each parameter being tested. Such instruments include the Beckman Coulter STKS or Gen-S Systems, the Abbott Cell-Dyn 4000 Hematology System, Bayer ADVIA 120, and the Sysmex XE2100 System. These improved automated instruments can measure one or more of: 1) reticulocytes, 2) red blood cells, 3) nucleated red blood cells, 4) platelets, 5) reticulated platelets, 6) white blood cells, including lymphocytes, monocytes, neutrophils, eosinophils, basophils, and 7) white blood cells with all phenotypes. It would thus be desirable to provide a hematology control composition that could be used as a control in connection with these instruments.

In the preferred embodiment, a hematology control composition for use with a multi-parameter automated hematology instrument includes a liquid suspension of particulates that has characteristics like whole blood. The control composition includes one or more blood cell components (i.e. components handled or treated to simulate such a component as found in whole blood), or their analogs, that may or may not be fixed, stabilized, or prepared by other treatment prior to final suspension. In different embodiments, the blood cell components or analog materials may be derived from a source that will exhibit the size, shape or other characteristics of human, animal, or other whole blood. By way of examples, U.S. Pat. Nos. 4,198,206; 4,436,821; 5,008,021; 5,262,327; 5,270,208; 5,432,089; 5,672,474; and 5,731,205, which are each hereby incorporated by reference, each contain examples of these types of blood cell components or analogs. The control has one or more blood component or analog to resemble corresponding components in whole blood when measured by the multi-parameter automated hematology instrument. When so measured, the control composition would assist in the calibration, operation, and accumulation of quality assurance data for the multi-parameter automated hematology instrument.

SUMMARY OF THE INVENTION

A hematology control and system for multi-parameter hematology measurement is provided. The hematology control provides values for the various components of blood that the multi-parameter hematology instrument is capable of measuring. The hematology control composition comprises components for simulating reticulocyte, white blood cell, red blood cell, nucleated red blood cell, platelet or reticulated platelet constituents of whole blood.

Methods of making and using the hematology control composition of the present invention are also provided herein.

The system of the present invention includes a hematology instrument, a control, and may further include output or readout devices. In one embodiment the system includes other peripheral devices, such as a device for tracking samples and associating them with particular data, such as a bar-code scanner system.

DETAILED DESCRIPTION OF THE PREFERRED EMBODIMENTS

The hematology control composition of the present invention comprises components for simulating one or more of the following constituents of whole blood: reticulocytes, white blood cells, red blood cells, nucleated red blood cells, platelets, or reticulated platelets. In one embodiment the components are suspended in an isotonic medium. The hematology control composition of the present invention provides values for various constituents of blood that a hematology instrument, such as a multi-parameter hematology instrument, is capable of measuring. Examples of multi-parameter hematology instruments include those available commercially without limitation, under the designations Beckman Coulter STKS or Gen-S Systems, the Abbott Cell-Dyn 4000 Hematology System, Bayer ADVIA 120 System, the Sysmex XE2100 System, or the like.

In one embodiment of the present invention, the reticulocyte component of the control composition comprises reticulocytes (that is, immature anucleate red blood cells containing some ribonucleic acid) or an analog thereof. For the present invention, the reticulocyte component is prepared in any suitable manner. By way of example, see U.S. Pat. No. 5,432,089, incorporated by reference. Among possible embodiments, the reticulocyte component may comprise true mammalian reticulocytes prepared for instance by mammalian (e.g. human) red blood cell encapsulation or by isolation from whole blood.

The white blood cell component of the hematology control composition comprises a blood cell (e.g. white blood cell) or analog thereof, selected from the group consisting of white blood cells for various cellular types, white blood cells for all phenotypes, and mixtures thereof. Among the possible embodiments, the white blood cell component may comprise white blood cells that are fixed with a suitable agent; preferably with an aldehyde; and more preferably glutaraldehyde, with glutaraldehyde and formaldehyde, or with 20% NuoSept 145. U.S. Pat. Nos. 5,270,208 and 5,262,327, incorporated herein by reference, provide examples of a suitable white blood cell component. Of course, the skilled artisan will appreciate that the subject invention is not limited to white blood cell components prepared from only white blood cells. Analogs prepared from any of a variety of other sources are possible, including but not limited to red blood cells from birds, reptiles, mammals, etc.

The red blood cell component comprises red blood cells or an analog thereof. Among other possible methods of preparation, the red blood cells may be washed free of all other cellular material, such as by using a magnesium gluconate diluent.

When employed, the nucleated red blood cell component of the control composition of the present invention comprises nucleated red blood cells or an analog thereof, such as avian red blood cells, e.g., turkey or chicken red blood cells.

In another embodiment of the present invention, the hematology control composition additionally provides a platelet component, preferably a simulated platelet component. Among other possible types, the platelet component may comprise stabilized human platelets or platelets simulated from goat, bovine or porcine blood cells. In one embodiment, they are prepared from red blood cells. See, U.S. Pat. Nos. 4,160,644 and 4,198,206, incorporated herein by reference, disclose an example of a suitable platelet reference control and methods of preparation. The skilled artisan will appreciate a number of other techniques for preparing simulated platelets.

In another embodiment of the present invention, the control composition comprises a reticulated platelet component. To illustrate, without limitation, goat red blood cells with encapsulated nucleic acids would constitute one example of a reticulated platelet component useful for the present invention.

The components of the control preferably are suspended in a suitable suspension medium that permits the control to be processed through the automated instrument. By way of example, among the possible embodiments of the present invention, the isotonic suspension medium may comprise a magnesium gluconate/ethylene diamine tetraacetic acid (EDTA)/phospate buffer with nucleated red blood cells; the same buffer with the additives HDL, sulfasalazine and alpha tocopherol; or the same buffer with 3% albumin.

The present invention further relates to a method of using the hematology control composition as set forth above in the analysis of whole blood. In addition, the present invention relates to a method of making a hematology control composition for use with multi-parameter systems, comprising the step of mixing one or more of a reticulocyte (retic) component, a white blood cell component, a red blood cell component, a nucleated red blood cell component, a platelet component, and a reticulated platelet component in an isotonic suspension medium.

It will be appreciated that the term "control composition" as used herein means one or more blood components and includes naturally occurring blood components as well as analogs thereof, which when combined or used alone, sufficiently simulate the relevant characteristics of whole blood for which the instrument tests. The following examples address the preparation of various of the constituent components. The control of the present invention contemplates an admixture of two or more of the components.

SPECIFIC EXAMPLE 1

The following example describes the preparation of a preferred control composition of the present invention.

Stock volumes of the constituent components are prepared in the following approximate concentrations:

| | |
|---|---|
| RBC: | $6.0 \times 10^6/mm^3$ |
| WBC: | $150,000/mm^3$ |
| Platelets: | $10 \times 10^6/mm^3$ |
| Retics: | 50% of $5.5 \times 10/mm^3$ red count |
| NRBC: | $0.5 \times 10^6/mm^3$ |

To prepare the final control composition, for example, in a 5 liter volume, stock volumes of the constituent components are combined as follows:

| | Approximate Target Count | Approximate Volume Stock |
|---|---|---|
| RBC: | $4.5 \times 10^6/mm^3$ | 3,750 ml |
| WBC: | $8.0 \times 10^3/mm^3$ | 266 ml |
| Plt (platelets) | $225 \times 10^3/mm^3$ | 112 ml |
| Retic (%) | 3% | 370 ml |
| NRBC | 0.01% | 4.5 ml |

The combined constituents are brought to a final total volume of 5 liters by adding final diluent including SUPERTRATE, prepared according to U.S. Pat. No. 5,262,327, incorporated herein. The skilled artisan will appreciate that there are other means and procedures to prepare this and other embodiments of the present invention.

SPECIFIC EXAMPLE 2

The following example describes the preparation of a preferred white blood cell component of the present invention.

In a preferred embodiment of the present invention, the white blood cells for cellular types comprise one or more of lymphocytes, monocytes, neutrophils, eosinophils and basophils. When preparing the white blood cell component for the control composition of the present invention, the cells are obtained by standard separation from whole blood or from portion of previously fractionated whole blood containing the desired cell population. The cells are resuspended, for instance, in a phosphate buffered solution containing polyethylene glycol 20,000 (PEG), EDTA and magnesium gluconate with 2% bovine serum albumin. The osmolarity of this solution is preferably sufficient to swell the white blood cells prior to fixation (e.g. about 215 mosm). The cells may then be stored in this solution, e.g. at about 6° C. for 1 hour.

The cells are fixed in a suitable media in order preferably to denature the surface or otherwise accomplish preserving the cell morphology. To illustrate, in one embodiment, in a solution of distilled water containing 5 g/l sorbitol, 7.4% formaldehyde and 0.125% glutaraldehyde. Of course, other suitable fixing agents may be used in suitable amounts. In a highly preferred embodiment, the white blood cells and the fix solution are maintained at a temperature sufficient to provide a proper white blood cell position (e.g. between about 4° C. and 12° C.). The fixative is added to the cells at a suitable ratio. For example, in one embodiment, a ratio of between 10 ml of cell suspension to 24 ml of fix solution is used. The distilled water in the fix solution swells the white blood cells further, while the fixative stabilizes the cell membrane. The cells are thus left in the fixative for 2 days at room temperature.

After fixation, the cells preferably are washed. In one aspect, they are washed in a phosphate buffered solution. One such solution contains PEG, EDTA, magnesium gluconate and bovine serum albumin. Lipoprotein concentrate is added at 150 mg/dl HDL to store the cells prior to use in order to improve the stability of the scattergram position while the white blood cells are waiting to be added to the other components of the control composition.

White blood cells prepared as described in U.S. Pat. No. 5,459,073 (incorporated herein by reference) for flow cytometry may be employed for phenotyping. By mixing the two types of white cells, both requirements can be met, i.e., white blood cells for various cellular types and phenotypes, as the cells prepared for phenotyping generally should not interfere with the position of other white blood cells on the histograms/scattergrams. For additional processing guidelines, see also U.S. Pat. Nos. 5,270,208, and 5,262,327, incorporated by reference herein. Of course analogs may be prepared from suitable red cells as the skilled artisan would appreciate.

SPECIFIC EXAMPLE 3

The following example describes the preparation of a preferred red blood cell component of the present invention.

In general, concentrated red blood cells are provided, separated from associated supernatant, and concentrated human red blood cell packs are suspended in a solution (e.g. phosphate buffered solution containing PEG (MW=20,000)) and allowed to settle overnight. The supernatant is then removed and 0.5% NaCl with PEG is added in an equal volume to the packed red blood cells and allowed to set at room temperature for 4–5 hours. The supernatant is again removed and the cells are resuspended in the NaCl solution and stored at 6° C. overnight. The packs are further checked for excessive hemolysis and removed from the inventory. The remaining packs are pooled into batches based on the (MCV'S), wherein twelve to fourteen packs are combined to make a batch. The batches are again resuspended in the NaCl solution for about 4–5 hours at room temperature. Of course, other times and temperatures may be employed.

Each batch is resuspended into a phosphate buffered solution containing PEG, EDTA and magnesium gluconate. The cells are allowed to settle, the supernatant is removed and the cells are resuspended in the above solution with lower PEG concentrations for storage up to 90 days at 6° C.

One diluent efficient in stabilizing the red blood cells on the Coulter STKS includes a phosphate buffered solution containing PEG, Na2EDTA, magnesium gluconate and sulfasalazine, wherein the sulfasalazine is added as an antioxidant to prevent hemolysis when the lipoprotein is added to the control composition of the present invention. The final diluent also contains 2% bovine serum albumin to improve the position of the white blood cells. After the cells have been washed into this diluent, trypsin inhibitor from soybeans is added at 0.06% to the total volume of red blood cells to give added stability to the MCV'S.

While the BSA in the diluent improves the white blood cell position on the scattergram, lipoprotein is also preferably used to provide a scattergram that represents whole blood. See U.S. Pat. Nos. 5,270,208 and 5,262,327 incorporated by reference. A lipoprotein source consisting of mostly HDL is added at about 100–175 mg/dl to the control composition and a-Tocopherol is further added to the lipoprotein source to reduce peroxides produced by the oxidation of the lipoproteins. If the lipoprotein source is added to the red blood cells without an antioxidant such as sulfasalazine or a-Tocopherol, the peroxides may cause hemolysis of the red blood cells in the present control composition.

SPECIFIC EXAMPLE 4

The following example describes the preparation of a nucleated red blood cell component of the present invention.

Turkey red blood cells are washed into a phosphate buffered solution and set to a count of about 1×106/mm3. The cells are fixed with a phosphate solution (volume equal to the cell volume)+0.4% v/v glutaraldehyde, at room temperature for one day and then washed into a phosphate buffer.

The fixed turkey red blood cells are added to the control composition of the present invention to yield a cell count equal to at least 10% of the white blood cell count in order to produce NRBC flags on the Coulter STKS or the Cell-Dyne 4000 manufactured by Abbott Laboratories. Though the present example contemplates the use of turkey cells, cells from other cell sources may be employed as the skilled artisan will appreciate.

SPECIFIC EXAMPLE 5

The following example describes the preparation of a simulated platelet component of the present invention.

Goat red blood cells are separated from other constituents of goat whole blood. For instance, cells are washed into PBS three times to remove the plasma and white cells. The concentration is adjusted to $8 \times 10^6$/mm3 and fixed with a volume of PBS equal to the cells that contain 0.224–0.320% glutaraldehyde, providing the amount of protection needed to allow proper lysis during the shrinkage step. The cells are incubated at 30° C. for one hour and centrifuged at 1200 RPM for 15 minutes. The supernatant is removed and the cell volume is adjusted to one-fourth of fixed volume.

An ammonium chloride solution is added to the cells to equal the original volume of fixed cells. The ammonium chloride solution creates holes in the membrane to allow hemoglobin to exit to the cells, while the glutaraldehyde protects from total lysis. The cells are monitored for hemoglobin loss based on (MPV) decreases on the H-1. When the MPV is at 10fl on the H-1, the cells are diluted with a phosphate buffered solution and centrifuged at 1800 RPM for 20 minutes. The supernatant is removed and the cells are washed to remove the free hemoglobin and shrink the membrane around the hemoglobin to produce an MPV of approximately 10fl on impedance instruments, such as the S+IV, manufactured by Beckman Coulter.

In a more preferred embodiment, to prevent further loss of hemoglobin and shrinkage of the membrane, the cells are fixed more than once, for instance, with 0.04% glutaraldehyde in a volume of phosphate buffered solution equal to the cell volume at a count of $1 \times 10^6$/mm3. The cells are left at room temperature overnight and then washed. Though the present example contemplates the use of goat cells, cells from other cell sources may be employed (such as stabilized human platelets) as the skilled artisan will appreciate.

SPECIFIC EXAMPLE 6

The following example describes the preparation of a reticulated platelet component of the present invention.

Preferably, reticulated platelets for the control composition of the present invention are prepared by washing goat red blood cells into 0.9% NaCl and concentrated to 70–80% HCT. Equal volumes of concentrated red blood cells and 4% RNA solution (20 mls of each) adjusted to 300 mosm with KCl are mixed together and dialyzed against 500 mls of a hypotonic solution containing glycerol (osm=90–100) for 90 minutes at 6° C. Dialysis is required to slowly change the osmolarity without damaging the cells. The resulting osmolarity change in the red blood cell solution is from about 300 mosm to about 150 mosm. This process creates holes in the cell membrane to allow the RNA in the red blood cell solution to enter the red blood cells.

The osmolarity is brought back to isotonicity by dialyzing the red blood cells containing RNA against an isotonic solution. This dialysis is at room temperature for 30 minutes and the final osmolarity of the cells is about 260 mosm. This process reseals the holes that were created by the hypotonic dialysis, thus trapping the RNA inside the cells.

Eighty milliliters of the resealing diluent containing 0.1% Nuosept 101 is added to the encapsulated red blood cells and the mixture is heated at 37° C. for 3 hours. This heating step helps to lyse the weakened cells from the encapsulation process and anneals the membranes of the encapsulated red blood cells.

SPECIFIC EXAMPLE 7

The following example describes a method using the control composition to determine the accuracy and reproducibility of the operation of a multi-parameter automated hematology instrument. By way of example, a multi-parameter automated hematology instrument, such as a Beckman Coulter STKS or Gen-S Systems, the Abbott Cell-Dyn 4000 Hematology System, Bayer ADVIA 120, and the Sysmex XE2100 System, is provided, optionally with a slide preparation module. The claimed control composition is obtained or prepared which includes, by way of example, a treated stabilized human red blood cell component and a reticulocyte component with quality control values in an appropriate range, for example, 1.0%, 2.5%, and 9.0%, respectively. It is refrigerated prior to use. At in the beginning of testing, the control composition is allowed to warm to room temperature for about fifteen minutes, mixed manually, and checked for resuspension of contents.

The control composition is prepared and analyzed by the same standard method as test samples which may be tested in batch quantities by the use of a suitable cassette having apertures for receiving test vials. After preparation, the control composition and test samples are analyzed by counting the population number of each subject component type with a multi-parameter automated hematology instrument, which will yield a visual display of the data.

For a Coulter System, the automated test instrument may employ technology known generally as VCS Technology (as marketed by Beckman Coulter). VCS generally analyzes cell samples in view of simultaneous volume conductivity and Scatter measurements. Ordinarily, a starting sample is employed in combination with suitable reagents (which may comprise a component of a kit) and physical agitation for lysing and cell measuring by way of flow cytometry.

Accordingly, the sample may be tested by the Coulter Principle of (DC) Impedance to measure the cell volume in an isotonic suspension.

Conductivity may be employed, for instance, by applying alternating current in the radio frequency range. Energy can penetrate the cell by short circuiting the cell membrane's bipolar lipid layer.

Information about the cells is also possible with light scatter techniques, such as from the scatter characteristics detected from cells in response to a coherent light source, e.g. a laser beam.

Of course, by no means is the mode of sample testing limited to the above. As mentioned other principles may be used.

The respective population counts obtained from the analysis are compared either to known reference value for each component type in the control composition, or by comparison of the population counts for each component types in the test sample with the corresponding values of components in the control composition. Data relating to the measurement of components in control composition and test samples is collected, monitored, stored, compared and analyzed by electronic means, such as a computer programmed with appropriate software and containing appropriate data file structure.

The foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

All patents and other publications cited herein are expressly incorporated by reference.

What is claimed is:

1. A hematology control composition comprising:
   a) a reticulocyte component;
   b) a white blood cell component;
   c) a red blood cell component;
   d) a nucleated red blood cell component;
   e) a platelet component; and
   f) a reticulated platelet component, mixed in an isotonic suspension medium.

2. The control composition of claim 1, wherein the reticulocyte component comprises reticulocytes or an analog thereof.

3. The control composition of claim 2, wherein the reticulocyte component comprises reticulocytes prepared by human red blood cell encapsulation.

4. The control composition of claim 2, wherein the reticulocyte component comprises reticulocytes prepared by isolation from whole blood.

5. The control composition of claim 1, wherein the white blood cell component comprises a member selected from the group consisting of white blood cells for cellular types, white blood cells for all phenotypes and mixtures thereof.

6. The control composition of claim 5, wherein the white blood cell component comprises a member selected from the group consisting of white blood cells that are stabilized with glutaraldehyde; with glutaraldehyde and formaldehyde; or with 20% NuoSept 145.

7. The control composition of claim 5, wherein the white blood cells for cellular types comprise:
   a) lymphocytes;
   b) monocytes;
   c) neutrophils;
   d) eosinophils; and
   e) basophils.

8. The control composition of claim 1, wherein the red blood cell component comprises human red blood cells.

9. The control composition of claim 1, wherein the nucleated red blood cell component comprises nucleated avian red blood cells.

10. The control composition of claim 9, wherein the nucleated avian red blood cells comprise turkey red blood cells.

11. The control composition of claim 1, wherein the platelet component comprises simulated platelets.

12. The control composition of claim 11, wherein the simulated platelets comprise goat red blood cells.

13. The control composition of claim 1, wherein the platelet component comprises human platelets.

14. The control composition of claim 1, wherein the reticulated platelet component comprises goat red blood cells.

15. A method of using the control composition of claim 1 to determine the accuracy and reproducibility of the operation of a multiparameter automated hematology instrument comprising the steps of:
   a) providing the hematology control composition of claim 1 with a known reference value for each component type;
   b) providing a multi-parameter automated hematology instrument;
   c) counting the population number per component type in the hematology control composition with the multi-parameter automated hematology instrument; and
   d) comparing the population number per component type obtained from step c) above with the known reference value for each component type.

16. A method of using the control composition of claim 1 in the analysis of whole blood comprising the steps of:
   a) providing the hematology control composition of claim 1 with a known reference value for each component type;
   b) providing a multi-parameter automated hematology instrument;
   c) providing one or more samples of whole blood;
   d) counting the population number per component type in the hematology control composition with the multi-parameter automated hematology instrument;
   e) counting the population number per component type in the whole blood sample with the multi-parameter automated hematology instrument; and
   f) comparing the population number per component in the hematology control composition obtained from step d) above with the population number per component in the whole blood sample obtained from step e) above.

17. The methods of claim 15 or 16, including means to collect, monitor, store, compare, and analyze data generated from the comparison of such control composition or test samples.

18. A method of making a hematology control composition for use with multi-parameter hematology measuring systems, comprising the step of mixing a reticulocyte component, a white blood cell component, a red blood cell component, a nucleated red blood cell component, a platelet component and a reticulated platelet component in an isotonic suspension medium.

19. The method of claim 18, wherein the reticulocyte component comprises reticulocytes or an analog thereof.

20. The method of claim 18, wherein the white blood cell component comprises a member selected from the group consisting of white blood cells for cellular types, white blood cells for all phenotypes and mixtures thereof.

21. The method of claim 20, wherein the white blood cells for cellular types comprise:
   a) lymphocytes;
   b) monocytes;
   c) neutrophils;
   d) eosinophils; and
   e) basophils.

22. The method of claim 18, wherein the red blood cell component comprises human red blood cells.

23. The method of claim 18, wherein the nucleated red blood cell component comprises nucleated avian red blood cells.

24. The method of claim 23, wherein the nucleated avian red blood cells comprise turkey red blood cells.

25. The method of claim 18, wherein the platelet component comprises simulated platelets.

26. The method of claim 25, wherein the simulated platelets comprise goat red blood cells.

27. The method of claim 18, wherein the reticulated platelet component comprises goat red blood cells.

28. A hematology control composition, comprising:
   a) a reticulocyte component;
   b) a white blood cell component including components corresponding with:
      i. lymphocytes;
      ii. monocytes;
      iii. neutrophils;
      iv. eosinophils; and
      v. basophils;
   c) a red blood cell component;
   d) a platelet component; and
   e) an isotonic suspension medium, wherein each of said components (a)–(d) is present in sufficient amounts to be measurable with an automated hematology instrument employing cell volume conductivity and scatter measurements to yield a readout that corresponds substantially with that of human whole blood.

29. A hematology control composition, comprising:
   a) a reticulocyte component;
   b) a white blood cell component;
   c) a red blood cell component;
   d) a platelet component; and
   e) an isotonic suspension medium, wherein each of said components (a)–(d) is present in sufficient amounts to be measurable with an automated hematology instrument and to yield a readout that corresponds substantially with that of human whole blood.

30. The control composition of claim 29 further comprising a reticulated platelet component.

31. The control composition of claim 30 further comprising a nucleated red blood cell component.

32. The control composition of claim 30 further comprising a source of lipoprotein.

* * * * *

Adverse Decision in Interference

Patent, No. 6,200,500

Wayne L. Ryan and John Scholl, HEMATOLOGY CONTROL AND SYSTEM FOR MULTI- PARAMETER HEMATOLOGY MEASUREMENTS, Interference 105,522, final judgment adverse to the patentees rendered, November 17, 2009, as to claims 1-31 of patent 6,221,668; 1-32 of patent 6,200,500; 1-20 of patent 6,399,388; 1-53 of patent 6,403,377; and claims 1-53 of patent 6,406,915.

*(Official Gazette March 24, 2020)*